(12) United States Patent
Hwang et al.

(10) Patent No.: US 11,911,060 B2
(45) Date of Patent: Feb. 27, 2024

(54) FORCEPS DRIVER APPARATUS

(71) Applicant: KOREA INSTITUTE OF SCIENCE AND TECHNOLOGY, Seoul (KR)

(72) Inventors: Donghyun Hwang, Seoul (KR); Sungwoo Park, Seoul (KR); Namseon Jang, Seoul (KR); Yong Seok Ihn, Seoul (KR); Jinwoo Jeong, Seoul (KR); Keehoon Kim, Seoul (KR); Sang Rok Oh, Seoul (KR); Sungwook Yang, Seoul (KR); Sehyuk Yim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 853 days.

(21) Appl. No.: 17/006,446

(22) Filed: Aug. 28, 2020

(65) Prior Publication Data

US 2021/0068858 A1 Mar. 11, 2021

(30) Foreign Application Priority Data

Sep. 5, 2019 (KR) .................. 10-2019-0109865

(51) Int. Cl.
*A61B 17/30* (2006.01)
*B25J 7/00* (2006.01)
(Continued)

(52) U.S. Cl.
CPC .............. *A61B 17/30* (2013.01); *B25J 7/00* (2013.01); *B25J 9/161* (2013.01); *B25J 9/1633* (2013.01);
(Continued)

(58) Field of Classification Search
CPC .......... A61B 17/30; A61B 2017/00398; A61B 2017/00017; A61B 2017/00345;
(Continued)

(56) References Cited

U.S. PATENT DOCUMENTS

| 4,753,235 | A | * | 6/1988 | Hasson | A61B 17/30 |
| | | | | | 606/206 |
| 7,988,215 | B2 | * | 8/2011 | Seibold | A61B 34/70 |
| | | | | | 606/205 |
| 2005/0033358 | A1 | | 2/2005 | Suzuki | |
| 2008/0103491 | A1 | * | 5/2008 | Omori | A61B 34/71 |
| | | | | | 606/1 |
| 2017/0112566 | A1 | * | 4/2017 | Volkmer | A61B 17/2909 |

FOREIGN PATENT DOCUMENTS

| FR | 3053267 A1 * | 1/2018 | ............. A61B 17/30 |
| JP | 2004350939 A | 12/2004 | |

(Continued)

*Primary Examiner* — Stephen A Vu
(74) *Attorney, Agent, or Firm* — Rabin & Berdo, P.C.

(57) ABSTRACT

Provided is a forceps driving apparatus including a body, a gripper installed to be received in the body and formed to be open and closed, an opening and closing member rotatably installed in the body to press or release two sides of the gripper by rotation, an elastic member connected to one side of the opening and closing member to provide an elastic force to the opening and closing member, an actuator connected to the other side of the opening and closing member to rotate the opening and closing member by contraction or extension, and a force sensing module to measure a gripping force of the gripper during the rotation of the opening and closing member.

11 Claims, 10 Drawing Sheets

(51) Int. Cl.
  *B25J 9/16* (2006.01)
  *B25J 13/08* (2006.01)
  *A61B 17/00* (2006.01)
  *A61B 90/00* (2016.01)

(52) U.S. Cl.
  CPC ... *B25J 13/085* (2013.01); *A61B 2017/00398* (2013.01); *A61B 2090/064* (2016.02)

(58) Field of Classification Search
  CPC ...... A61B 2017/2926; A61B 2017/305; A61B 2090/064; A61B 17/282; A61B 17/29; A61B 34/72; A61B 34/76; A61B 90/06; B25J 7/00; B25J 9/161; B25J 9/1633; B25J 13/085
  See application file for complete search history.

(56) References Cited

FOREIGN PATENT DOCUMENTS

| | | | |
|---|---|---|---|
| JP | 2006-239279 A | 9/2006 | |
| JP | 4938156 B2 * | 5/2012 | ....... A61B 17/00234 |
| JP | 2016034342 A | 3/2016 | |
| KR | 10-0665667 B1 | 1/2007 | |
| KR | 10-1388069 B1 | 4/2014 | |
| KR | 101633919 B1 | 6/2016 | |
| KR | 10-2016063 B1 | 8/2019 | |
| KR | 10-2020-0003653 A | 1/2020 | |

* cited by examiner

FORCEPS DRIVER APPARATUS

DESCRIPTION OF GOVERNMENT-FUNDED RESEARCH AND DEVELOPMENT

This research is conducted by Korea Institute of Science and Technology, and funded by STEAM research (system integration and testing of bionic arm with biosignal based control function, No. 1711097690) of National Research Foundation of Korea, Ministry of Science and ICT, Republic of Korea.

CROSS-REFERENCE TO RELATED APPLICATION

This application claims priority to Korean Patent Application No. 10-2019-0109865, filed on Sep. 5, 2019, and all the benefits accruing therefrom under 35 U.S.C. § 119, the contents of which in its entirety are herein incorporated by reference.

BACKGROUND

1. Field

The present disclosure relates to a forceps driver apparatus, and more particularly, to a forceps driver apparatus for controlling a microgripping force of a gripper.

2. Description of the Related Art

A device, in which two wheels positioned on top of linear sliders driven by an electric motor operate in the lengthwise direction of forceps, and grip of the forceps is enabled by the operation, is well known.

This device needs to change the stroke of the motor and the length of the linear slider to drive forceps having different lengths.

It is necessary to push commercially available forceps from the top of the device toward the bottom to mount the forceps, and when the forceps is mounted by this method, it is impossible to separately make use of the top space.

In addition, the device cannot measure a gripping force, failing to control a microforce.

SUMMARY

The present disclosure is directed to providing a device for opening and closing forceps without changing the stroke of a motor or the length of a linear slider.

The present disclosure is directed to providing a device for controlling a microgripping force of a gripper.

To solve the above-described problem, a forceps driving apparatus of the present disclosure includes a body, a gripper installed to be received in the body and formed to be open and closed, an opening and closing member rotatably installed in the body to press or release two sides of the gripper by rotation, an elastic member connected to one side of the opening and closing member to provide an elastic force to the opening and closing member, an actuator connected to the other side of the opening and closing member to rotate the opening and closing member by contraction or extension, and a force sensing module to measure a gripping force of the gripper during the rotation of the opening and closing member.

According to an example related to the present disclosure, the force sensing module may include a sensor to measure a force transmitted when the opening and closing member presses or releases the two sides of the gripper, and a printed circuit board (PCB) to supply the sensor with power and receive and output information associated with the force measured by the sensor.

The force sensing module may further include a stress transmitter installed on one surface of the PCB and having a receiving portion in which the sensor is installed, to transmit the force when the opening and closing member presses or releases the two sides of the gripper to the sensor.

The gripping force of the gripper generated when the opening and closing member presses or releases the two sides of the gripper may be calculated by calibrating the force measured by the sensor.

According to another example related to the present disclosure, the forceps driving apparatus of the present disclosure may further include a control unit to control the operation of the actuator, and the control unit may include a fuzzy controller to output proportional-integral-derivative (PID) gains, and a PID controller to receive inputs of the PID gains from the fuzzy controller, output an amount of control and drive the actuator based on the amount of control.

The control unit may further include a limiter to limit the output of the amount of control to prevent the amount of control from being determined in a range in which the amount of control is larger than a predetermined amount or there is no responsiveness, and a force feedback unit to feed back a force changed by the operation of the actuator to the fuzzy controller and the PID controller.

In an initial condition, the opening and closing member may press the gripper by the elastic force of the elastic member to close the gripper, and in an operating condition, the opening and closing member may release the gripper by the contraction of the actuator to open the gripper.

The gripper may include a first part having a first grasping end formed at one end, and a second part having a second grasping end formed at one end and elastically connected to the other end of the first part, and one end of the first and second parts may be closed when pressed by the opening and closing member, and may be open when released by the opening and closing member.

The opening and closing member may include a guide pin rotatably installed in the body, a rotating plate connected to the guide pin, and a pressing member formed at each of two sides of the rotating plate to press the first and second parts.

A bearing may be installed between the body and the guide pin.

One of the pressing members may have a fixing groove and one end of the elastic member may be wound on the fixing groove to provide the elastic force to the pressing member, and the other pressing member may have a fixing hole and one end of the actuator may be installed in the fixing hole to provide torque to the opening and closing member.

According to still another example related to the present disclosure, in the initial condition, each pressing member may press each of the first and second parts by the elastic force of the elastic member to close the ends of the first and second parts, and in the operating condition, each pressing member may release each of the first and second parts by the contraction of the actuator to open the ends of the first and second parts.

DETAILED DESCRIPTION

Hereinafter, the disclosed embodiments will be described in detail with reference to the accompanying drawings, and identical or similar elements are given identical or similar reference signs and redundant descriptions are omitted herein. As used herein, the suffix "unit" is only given or used to ease the drafting of the specification, and does not have any meaning or role for identifying itself. Additionally, in describing the embodiments disclosed herein, when it is determined that a certain detailed description of relevant known technology may make the key subject matter of the disclosed embodiments ambiguous, the detailed description is omitted herein. Additionally, the accompanying drawings are provided for an easy understanding of the disclosed embodiments, and the technical spirit disclosed herein is not limited by the accompanying drawings, and it should be understood that the present disclosure covers all modifications, equivalents or substitutes falling in the spirit and technical scope of the present disclosure.

The terms "first", "second", and the like may be used to describe various elements, but the elements are not limited by the terms. These terms are used to distinguish one element from another.

It will be understood that when an element is referred to as being "connected to" another element, the element can be connected to the other element, but intervening elements may be present.

Unless the context clearly indicates otherwise, the singular forms include the plural forms as well.

It should be understood that the term "comprises" or "includes" when used in this specification, specifies the presence of stated features, integers, steps, operations, elements, components or groups thereof, but does not preclude the presence or addition of one or more other features, integers, steps, operations, elements, components, or groups thereof.

Figure 1A:
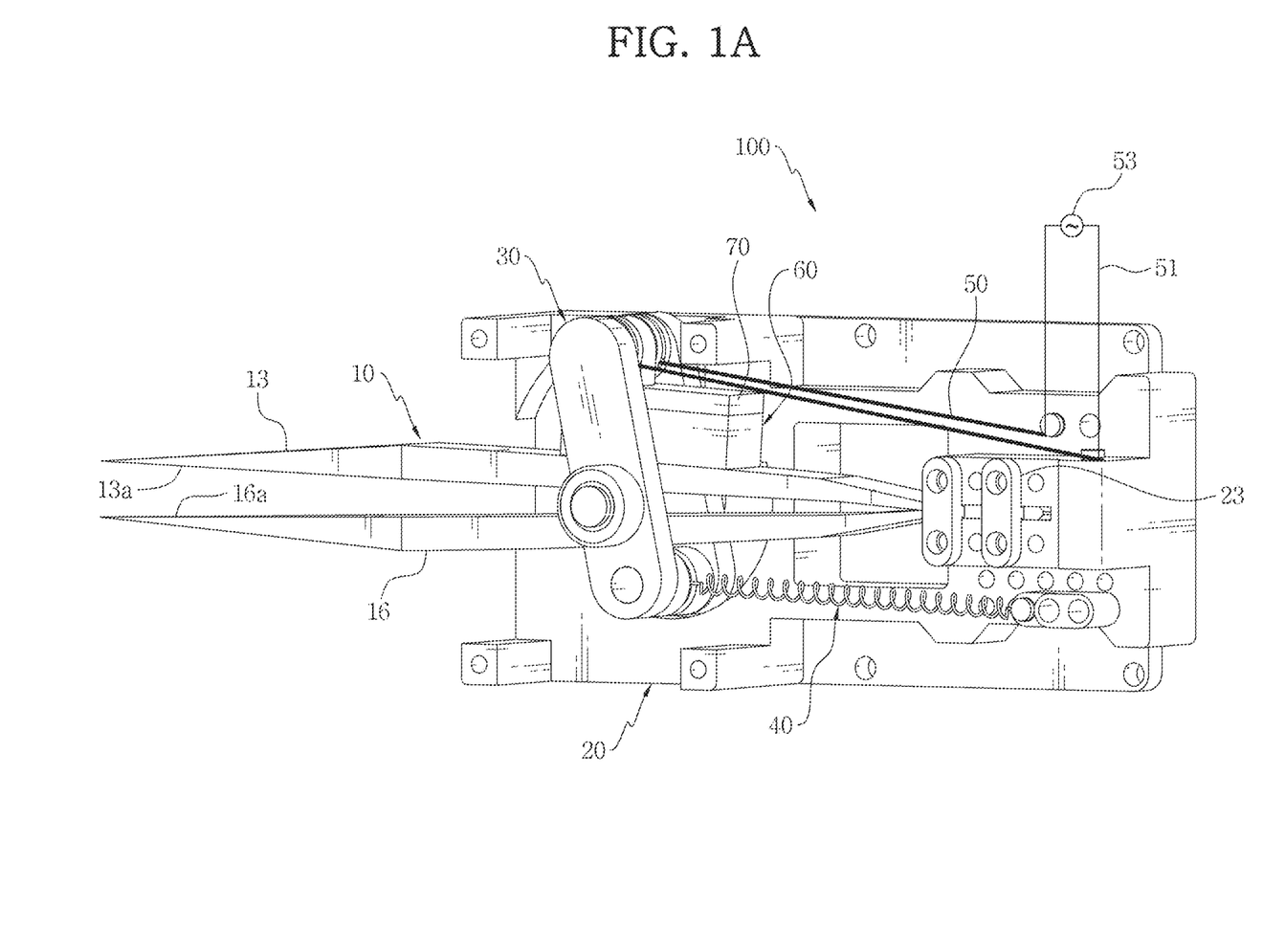
FIG. 1A is a perspective view showing an example of a forceps driving apparatus of the present disclosure.
Figure 1B:
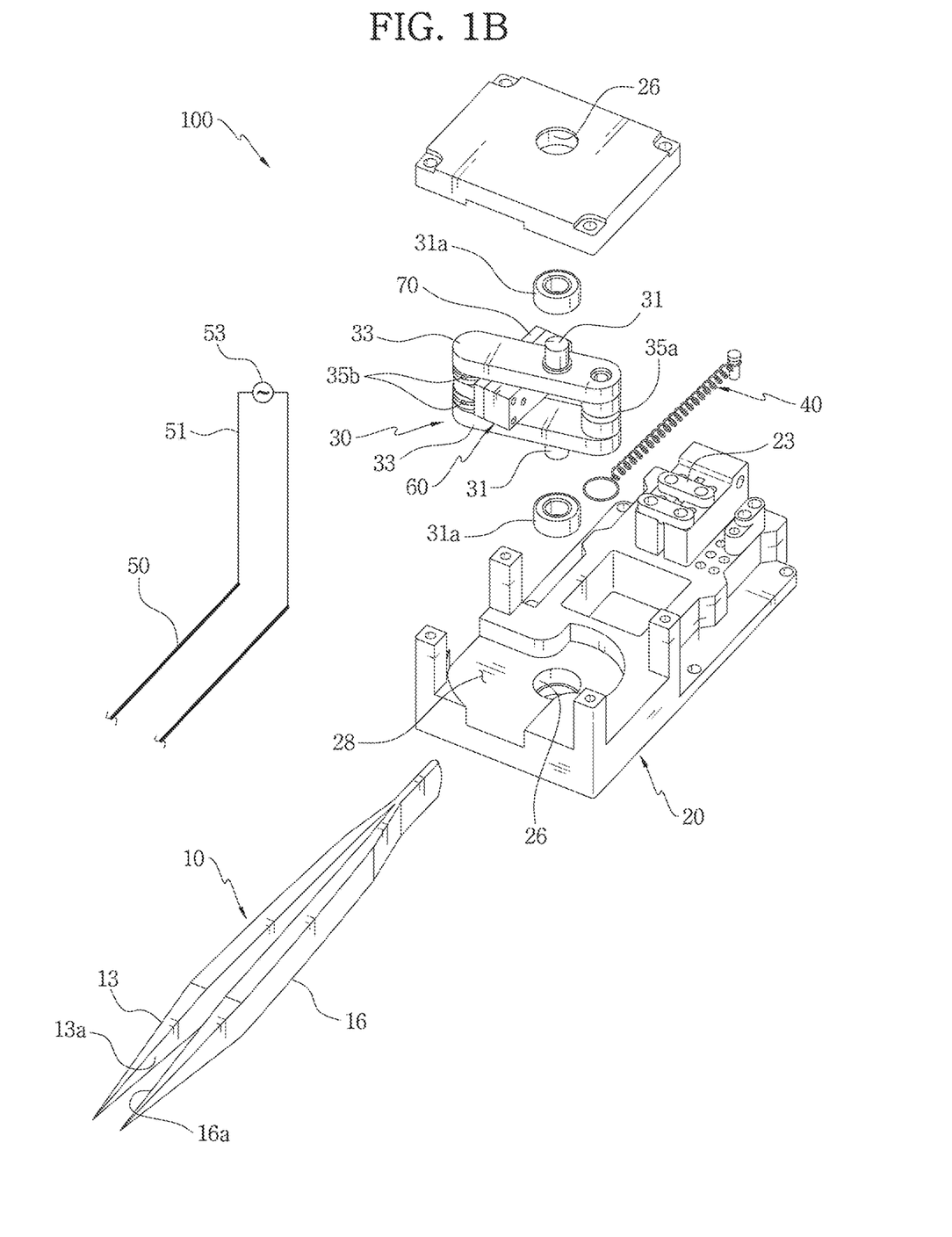
FIG. 1B is an exploded perspective view showing an example of a forceps driving apparatus of the present disclosure.
Figure 1C:
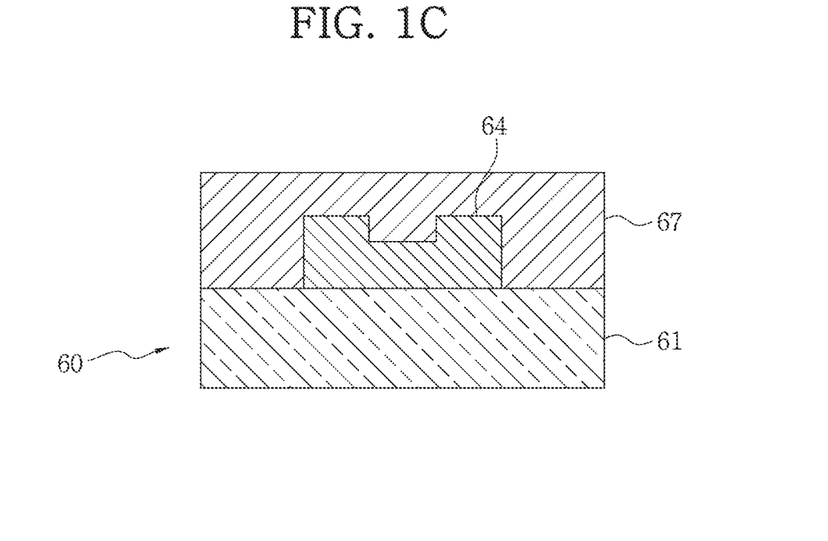
FIG. 1C is a cross-sectional view showing the structure of a force sensing module of FIG. 1A.
Figure 1D:
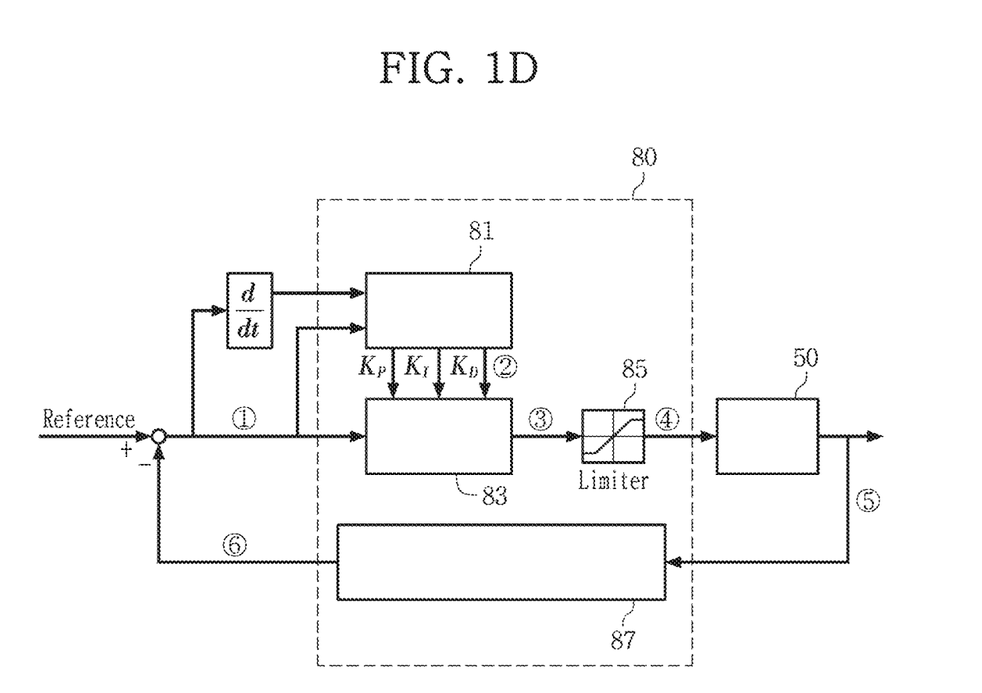
FIG. 1D is a conceptual view showing a configuration and operation of a control unit of the present disclosure.

FIG. 1A is a perspective view showing an example of a forceps driving apparatus 100 of the present disclosure, and FIG. 1B is an exploded perspective view showing an example of the forceps driving apparatus 100 of the present disclosure. FIG. 1C is a cross-sectional view showing the structure of a force sensing module 60 of FIG. 1A, and FIG. 1D is a conceptual view showing a configuration and operation of a control unit 80 of the present disclosure.

Figure 1E:
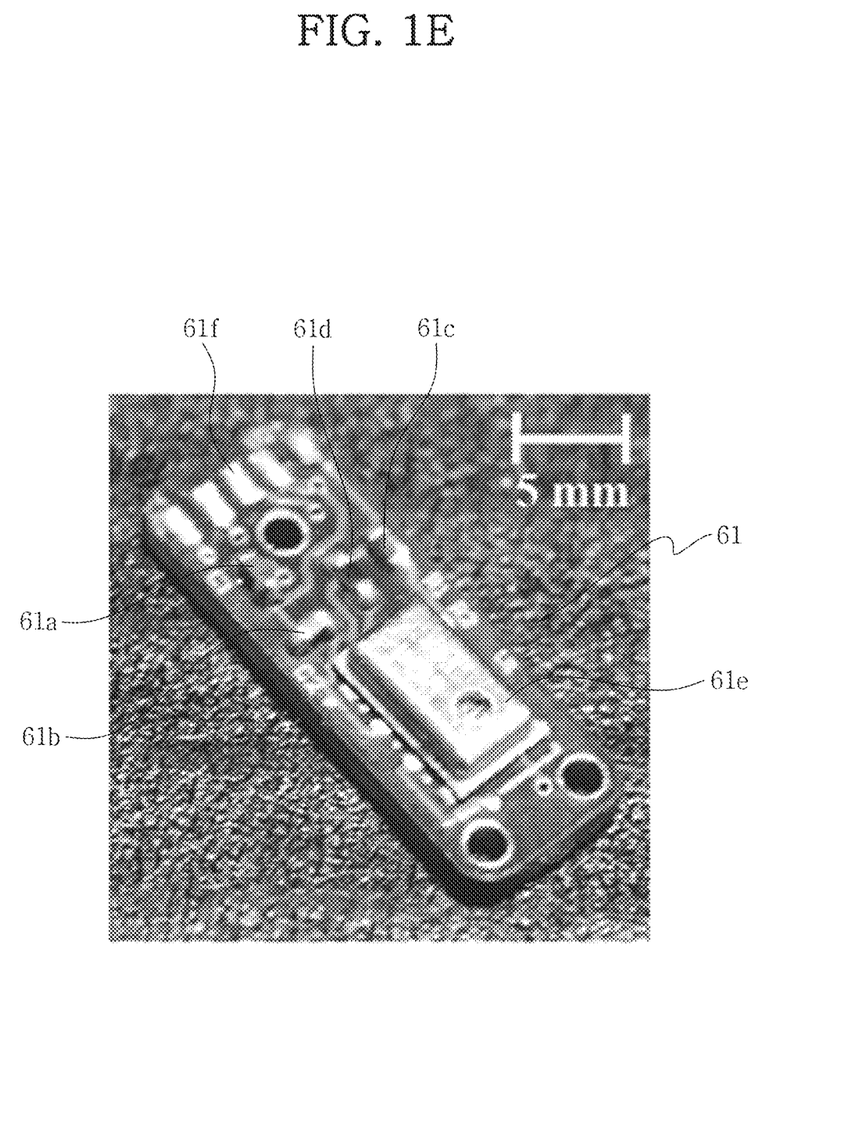
FIG. 1E is a perspective view showing a configuration of a printed circuit board (PCB) of the present disclosure.
Figure 1F:
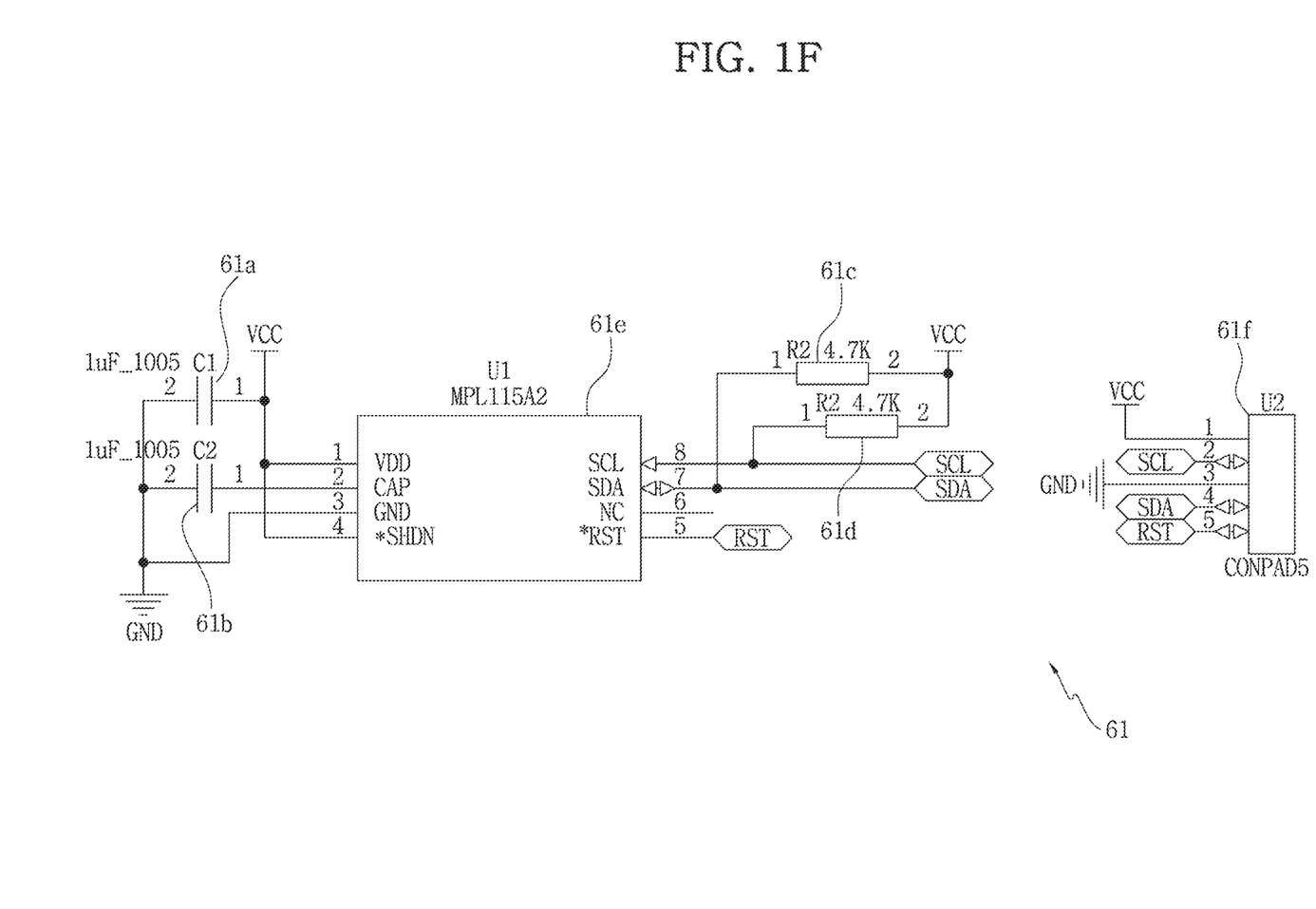
FIG. 1F is a circuit diagram of the PCB of FIG. 1E.
Figure 3A:
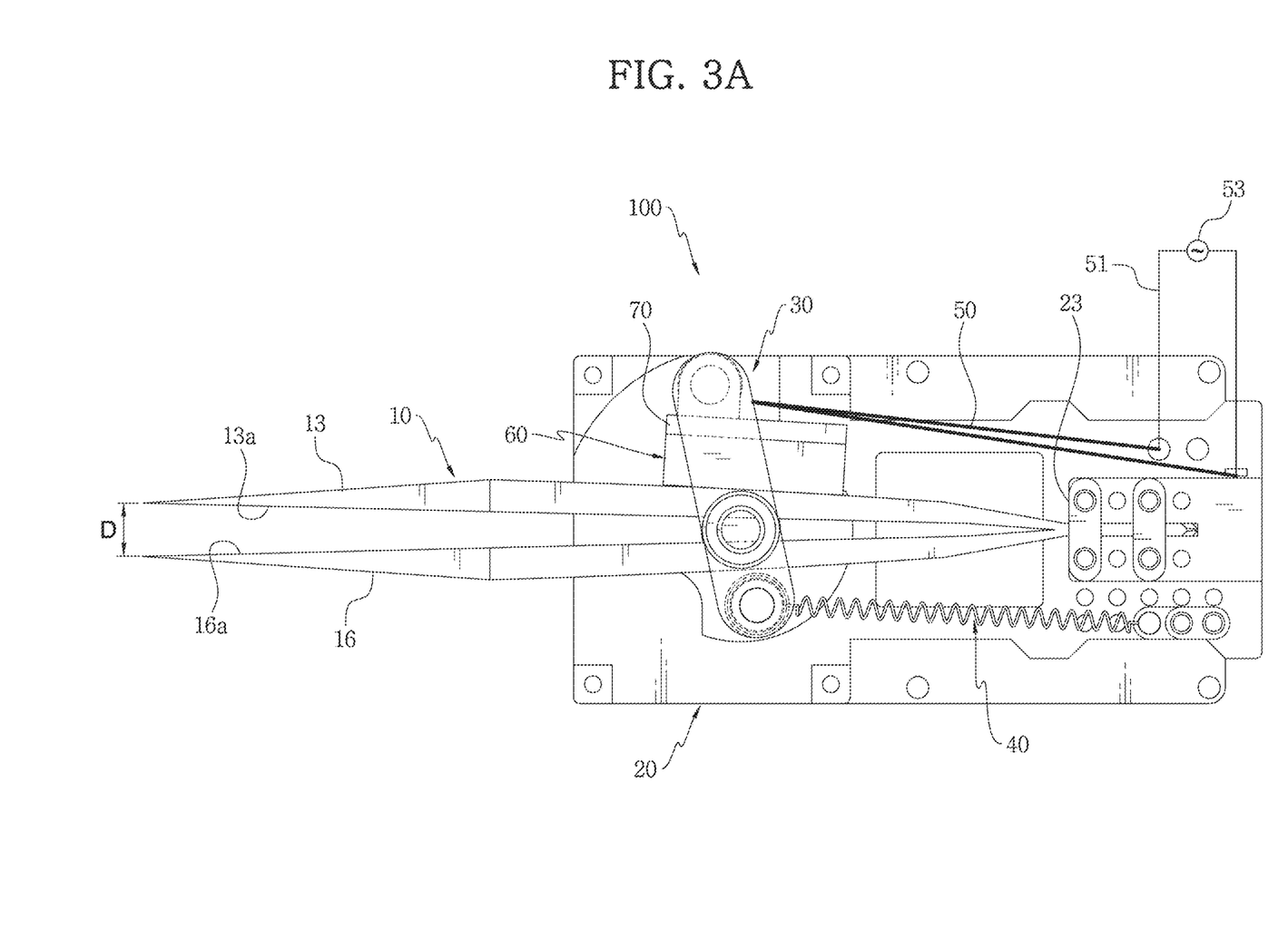
FIG. 3A is a plane view showing an operation of a forceps driving apparatus of the present disclosure.
Figure 3B:
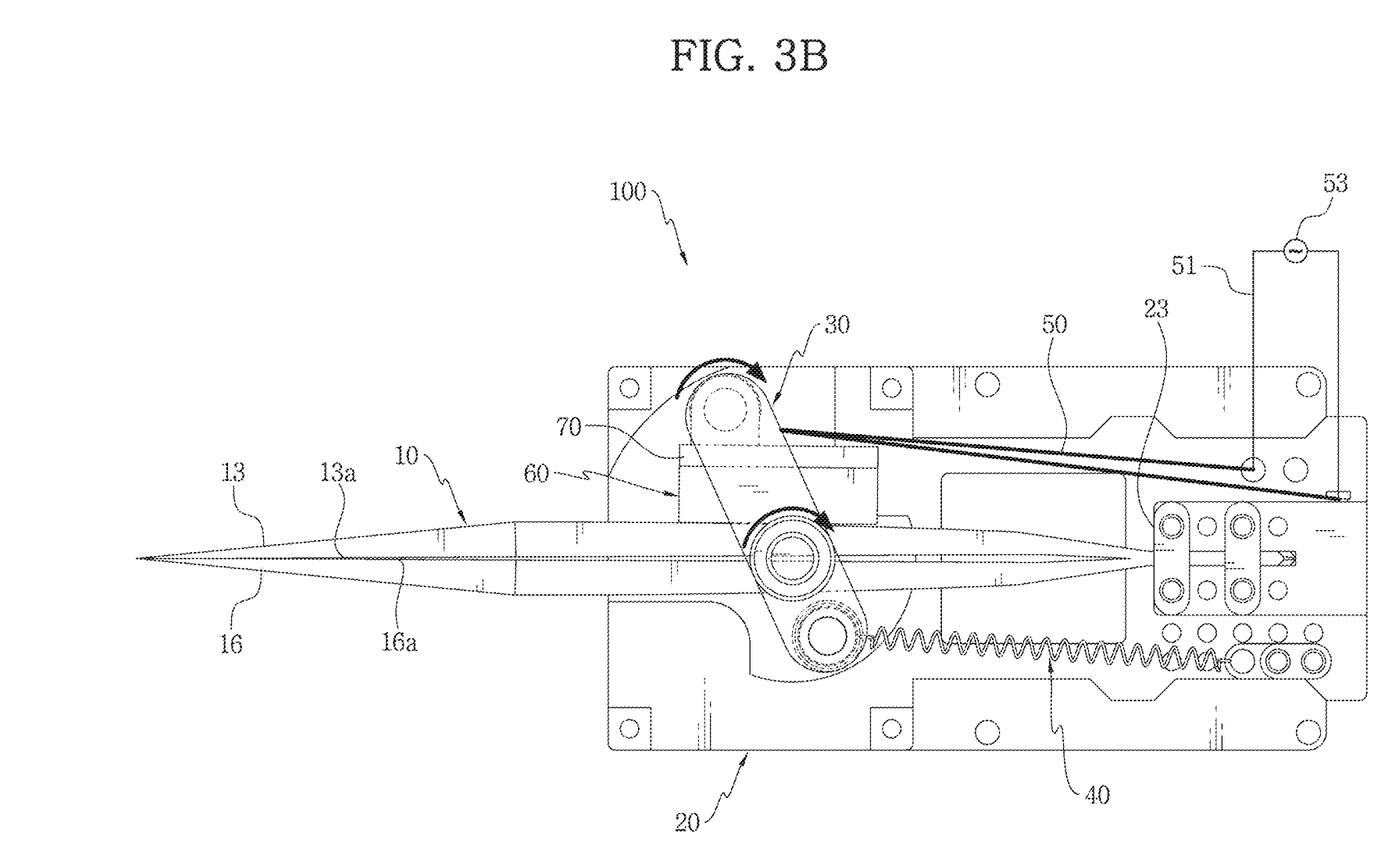
FIG. 3B is a plane view showing another operation of a forceps driving apparatus of the present disclosure.

Additionally, FIG. 1E is a perspective view showing a configuration of a printed circuit board (PCB) 61 of the present disclosure, and FIG. 1F is a circuit diagram of the PCB 61 of FIG. 1E. Meanwhile, FIG. 3A is a plane view showing an operation of the forceps driving apparatus 100 of the present disclosure, and FIG. 3B is a plane view showing another operation of the forceps driving apparatus 100 of the present disclosure.

Referring to FIGS. 1A and 1B, the forceps driving apparatus 100 of the present disclosure includes a gripper 10, a body 20, an opening and closing member 30, an elastic member 40, an actuator 50 and the force sensing module 60.

The gripper 10 is deformed to be open and closed. Additionally, the gripper 10 is installed in the body 20 such that the gripper 10 is received by the body 20. In the present disclosure, opening and closing of the gripper 10 may be understood as allowing one end of the gripper 10 to grasp or release the tissue or skin.

The gripper 10 may be formed with a structure in which one end is open and closed. For example, the gripper 10 may be forceps or surgical scissors, and FIG. 1A shows an example in which the gripper 10 is forceps.

The body 20 is formed to receive the gripper 10. Additionally, the body 20 may include a gripper holder 23 to couple the gripper 10. FIG. 1A shows an example in which the right end of the gripper 10 is coupled to the gripper holder 23, and the gripper 10 is installed in the body 20 such that the gripper 10 is received in the body 20 while being open and closed.

The opening and closing member 30 is rotatably installed in the body 20 to press or release two sides of the gripper 10.

When the opening and closing member 30 presses the two sides of the gripper 10 in one direction, the end of the gripper 10 may be closed, and in the releasing condition, the opening and closing member 30 may move away from the gripper 10 in one direction, and the gripper 10 may be open.

The elastic member 40 is connected to one side of the opening and closing member 30 to provide an elastic force to the opening and closing member 30. The elastic member 40 may be, for example, a spring. FIG. 1A shows an example in which one end of the elastic member 40 is bolt-connected to the body 20, and the other end is connected to one side of the opening and closing member 30.

The actuator 50 is connected to the other side of the opening and closing member 30 to rotate the opening and closing member 30 by contraction or extension. The actuator 50 may be made of, for example, a shape memory alloy (SMA) that contracts when subjected to heat of a predetermined temperature. Additionally, the actuator 50 may be formed in the shape of a wire.

Referring to FIG. 1A, shown is an example in which the elastic member 40 is installed in the opening and closing member 30 below the gripper 10, and the actuator 50 is installed in the opening and closing member 30 above the gripper 10. Additionally, FIG. 1A shows an example in which a power supply 53 that supplies the actuator 50 with power is connected to the actuator 50 via an electrical wire 51. However, in the present disclosure, the arrangement relationship between the elastic member 40 and the actuator 50 and the connection relationship of the power supply 53 connected to the actuator 50 with the electrical wire 51 are not necessarily limited thereto.

The force sensing module 60 may measure a gripping force during the operation of the opening and closing member 30. Referring to FIG. 1C, the force sensing module 60 may include the PCB 61, a sensor 64 and a stress transmitter 67.

The PCB supplies the sensor 64 with power, and receives and outputs information associated with a force measured by the sensor 64.

FIG. 1E is a perspective view showing the configuration of the PCB 61 of the present disclosure, and FIG. 1F is a circuit diagram of the PCB 61 of FIG. 1E.

Referring to FIGS. 1E and 1F, for example, the PCB 61 may include two capacitors 61a, 61b to stabilize power applied from the outside, two resistors 61c, 61d to pull up I2C communication data and clock line respectively, a pressure sensor 61e to measure the pressure and a con pad to enable connection to an external device.

The two capacitors 61a, 61b may be each 1 μm, and the two resistors 61c, 61d may be each 4.7 KΩ.

The sensor 64 may measure the force transmitted when the opening and closing member 30 presses or releases the two sides of the gripper 10. The sensor 64 is installed on one surface of the PCB 61 and electrically connected to the PCB 61.

For example, the sensor 64 may be a manometer to measure the atmospheric pressure, and in this case, the sensor 64 may be the pressure sensor 61e of FIGS. 1E and 1F.

The stress transmitter 67 is installed on one surface of the PCB 61, and has a receiving portion in which the sensor 64 is installed in contact. The stress transmitter 67 may be made of an elastic material to transmit the force when the opening and closing member 30 presses or releases the two sides of the gripper 10 to the sensor 64.

The stress transmitter 67 may be made of urethane, but is not necessarily limited thereto, and may be made of any material capable of transmitting the force transmitted when the opening and closing member 30 presses or releases the two sides of the gripper 10 to the sensor 64.

The stress transmitter 67 may be installed on the PCB 61 by casting and curing. In the casting process, the stress transmitter 67 may remove the remaining air from the stress transmitter 67 or the sensor 64 through a pump. Additionally, the stress transmitter 67 may be installed in contact with the sensor 64 by curing for 24 hours.

A gripping force of a first part 13 of the gripper 10 may be calculated by calibrating the force measured by the sensor 64.

The forceps driving apparatus 100 of the present disclosure may further include a support plate 70 fixedly installed in contact with the force sensing module 60 to transmit a rotational force of the opening and closing member 30 to the force sensing module 60 to rotate the force sensing module 60.

The support plate 70 contacts the force sensing module 60, and FIG. 1A shows an example in which the support plate 70 is installed in contact with the force sensing module 60 between two rotating plates.

The support plate 70 supports the force sensing module 60 to transmit the rotational force from the opening and closing member 30 to the force sensing module 60.

FIG. 1D is a conceptual view showing the configuration and operation of the control unit 80 of the present disclosure.

Referring to FIG. 1D, the forceps driving apparatus 100 of the present disclosure may further include the control unit 80 to control the operation of the actuator 50.

The control unit 80 may include a fuzzy controller 81, a proportional-integral-derivative (PID) controller 83, a limiter 85 and a force feedback unit 87.

The fuzzy controller 81 receives inputs of an error corresponding to a difference between a reference and a feedback loop and a derivation of error, and outputs PID gains through fuzzification, rule-base and defuzzification.

The PID controller 83 receives the PID gains from the fuzzy controller 81, outputs the amount of control by multiplying the gains by the error, the accumulated error and the derivation of error, and drives the actuator 50 based on the amount of control.

The limiter 85 limits the output of the amount of control to prevent the amount of control from being determined in the range in which the amount of control is too large or there is nearly no responsiveness.

For example, the fuzzy controller 81, the PID controller 83 and the limiter 85 may be each mounted in a micro controller unit (MCU).

The force feedback unit 87 may feed back the force generated by the rotation of the opening and closing member 30 measured by the sensor 64 and the force changed by the operation of the actuator 50 to the fuzzy controller 81 and the PID controller 83.

As shown in FIG. 1D, the control process performed by the control unit 80 of the present disclosure will be described.

An input target force and the current force obtained through the sensor 64 are compared and transmitted to the fuzzy controller 81 and the PID controller 83 (①). Subsequently, the input error (e) and derivation of error (de) are converted to P, I, D gains (Kp, KI, KD) to be used by the PID controller through the fuzzy controller 81 (②). Subsequently, an amount of control (pulse width modulation (PWM) voltage duty) to control is outputted through e and PID gains received from the PID controller 83 (③). Subsequently, the limiter 85 limits the output of the amount of control to prevent the overheat and failure of the actuator 50 when the amount of control exceeds a predetermined amount (④). Subsequently, the actuator 50 operates through the amount of control outputted from the controller (⑤). Subsequently, the force feedback unit 87 feeds back the changed force (⑥).

In the forceps driving apparatus 100 of the present disclosure, for example, in the initial condition, referring to FIG. 3A, when the opening and closing member 30 presses the gripper 10 by the elastic force of the elastic member 40, the gripper 10 may be closed, and in the operating condition, referring to FIG. 3B, when the gripper 10 is released from the opening and closing member 30 by the contraction of the actuator 50, the gripper 10 may be open.

However, the present disclosure is not necessarily limited to this operation, and an example is possible in which the gripper 10 is open in the initial condition, and the gripper 10 is closed by the operation of the actuator 50 in the operating condition.

Referring to FIGS. 1A and 1B, the gripper 10 may include the first part 13 and a second part 16.

The first part 13 may have a first grasping end 13a at one end. The second part 16 may be elastically connected to the other end of the first part 13. The second part 16 has a second grasping end 16a at one end to make an opening or closing motion with the first grasping end 13a.

FIGS. 1A and 1B show an example in which the first and second parts 13, 16 form the two sides of the gripper 10. Additionally, referring to FIG. 1A, shown is an example in which the gripper 10 is coupled to the gripper holder 23, and the gripper holder 23 is installed in the body 20. As shown in FIGS. 1A and 1B, the first and second parts 13, 16 may be formed with a slant at the area coupled to the gripper holder 23 to make it easy to be pressed by the opening and closing member 30.

Additionally, as best shown in FIG. 1B, the opening and closing member 30 may include a guide pin 31, a rotating plate 33 and a pressing member 35.

The guide pin 31 may be rotatably installed in the body 20. The guide pin 31 may act as an axis of rotation in the rotation of the rotating plate 33. A bearing 31a may be further installed between the guide pin 31 and the body 20. The outer periphery of the bearing 31a may be coupled to the body 20, and the inner periphery of the bearing 31a may be coupled to the outer periphery of the guide pin 31, thereby improving the abrasion resistance of the guide pin 31 and allowing rotation relative to the body 20. Referring to FIG. 1B, shown is an example in which the body 20 has a bearing coupling hole 26 in which the bearing 31a is installed.

The rotating plate 33 may be connected to the guide pin 31. Additionally, the rotating plate 33 may be placed on one surface of the gripper 10. The pressing member 35 may be formed at each of two sides of the rotating plate 33, and the pressing members 35 may press the first and second parts 13, 16.

Additionally, the body 20 may include a rotation receiving member 28 to receive the guide pin 31 and the pressing member 35. The rotation receiving member 28 may be recessed along the rotational movement path of the pressing member 35 on one surface of the inner part of the body 20 within which the gripper 10 reaches.

Meanwhile, one of the pressing members 35 has a fixing groove 35a, and the fixing groove 35a may be formed along the circumferential direction on the outer periphery of the pressing member. One end of the elastic member 40 may be formed in the shape of a hook which is wound on the fixing groove 35a.

The other pressing member 35 has a fixing hole 35b, and one end of the actuator 50 may be installed in the fixing hole 35b to provide torque to the opening and closing member 30. For example, one end of the actuator 50 may be installed and inserted into a plurality of fixing holes 35b. Shown is an example of the opening and closing member 30 of FIG. 1B having the fixing groove 35a formed in the left pressing member 35 and the fixing hole 35b formed in the right pressing member 35.

In the initial condition, referring to FIG. 3A, the pressing members 35 on two sides of the rotating plate 33 may press each of the first and second parts 13, 16 by the elastic force of the elastic member 40 to close the first and second grasping ends 13a, 16a.

Meanwhile, in the operating condition, referring to FIG. 3B, when the actuator 50 contracts, each pressing member 35 may release each of the first and second parts 13, 16 to open the first and second grasping ends 13a, 16a.

However, the present disclosure is not necessarily limited to this operation, and an example is possible in which the gripper 10 is open in the initial condition, and the gripper 10 is closed by the operation of the actuator 50 in the operating condition.

Figure 2A:
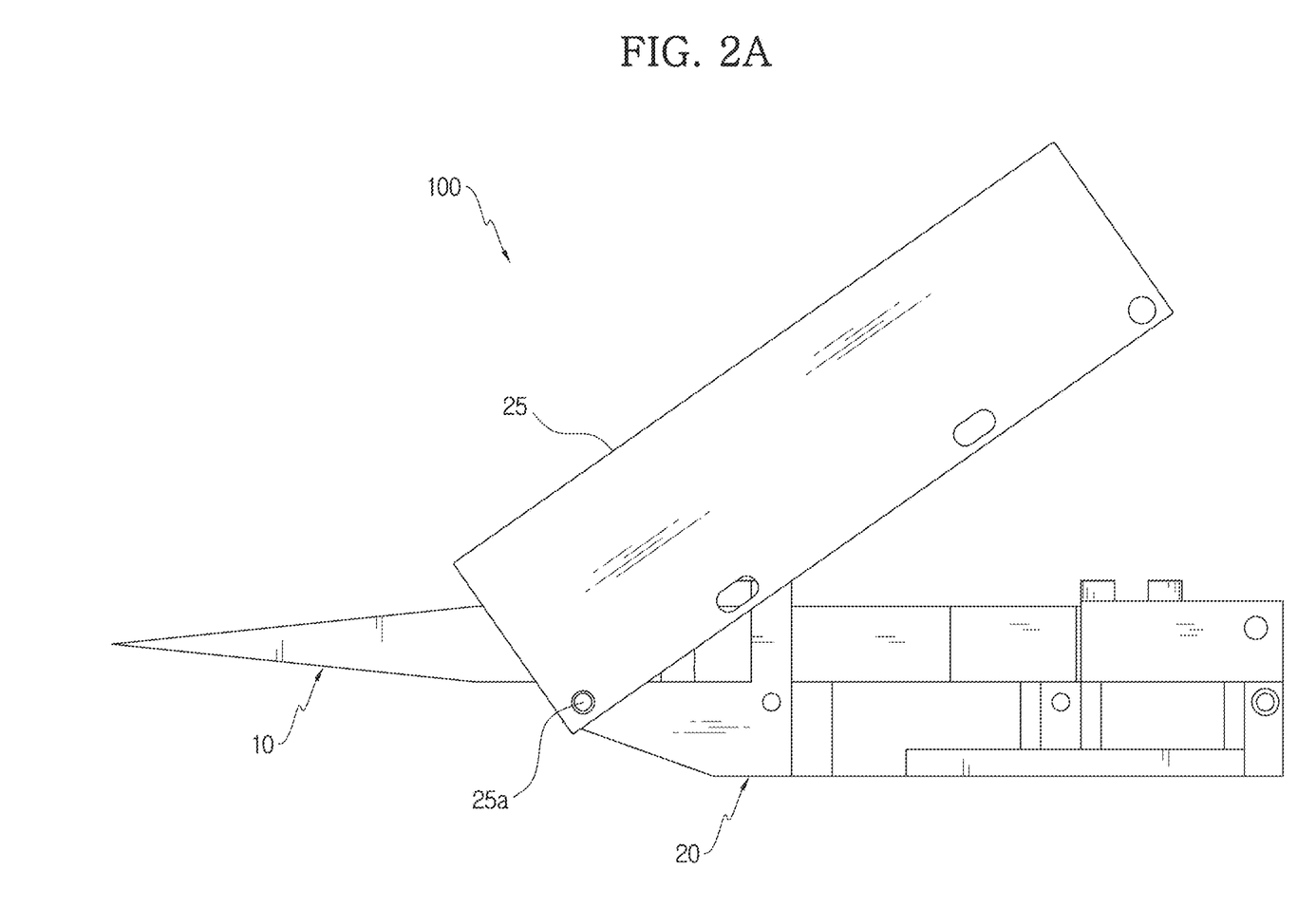
FIG. 2A is a side view showing an example of operation of a forceps driving apparatus of the present disclosure including a cover.
Figure 2B:
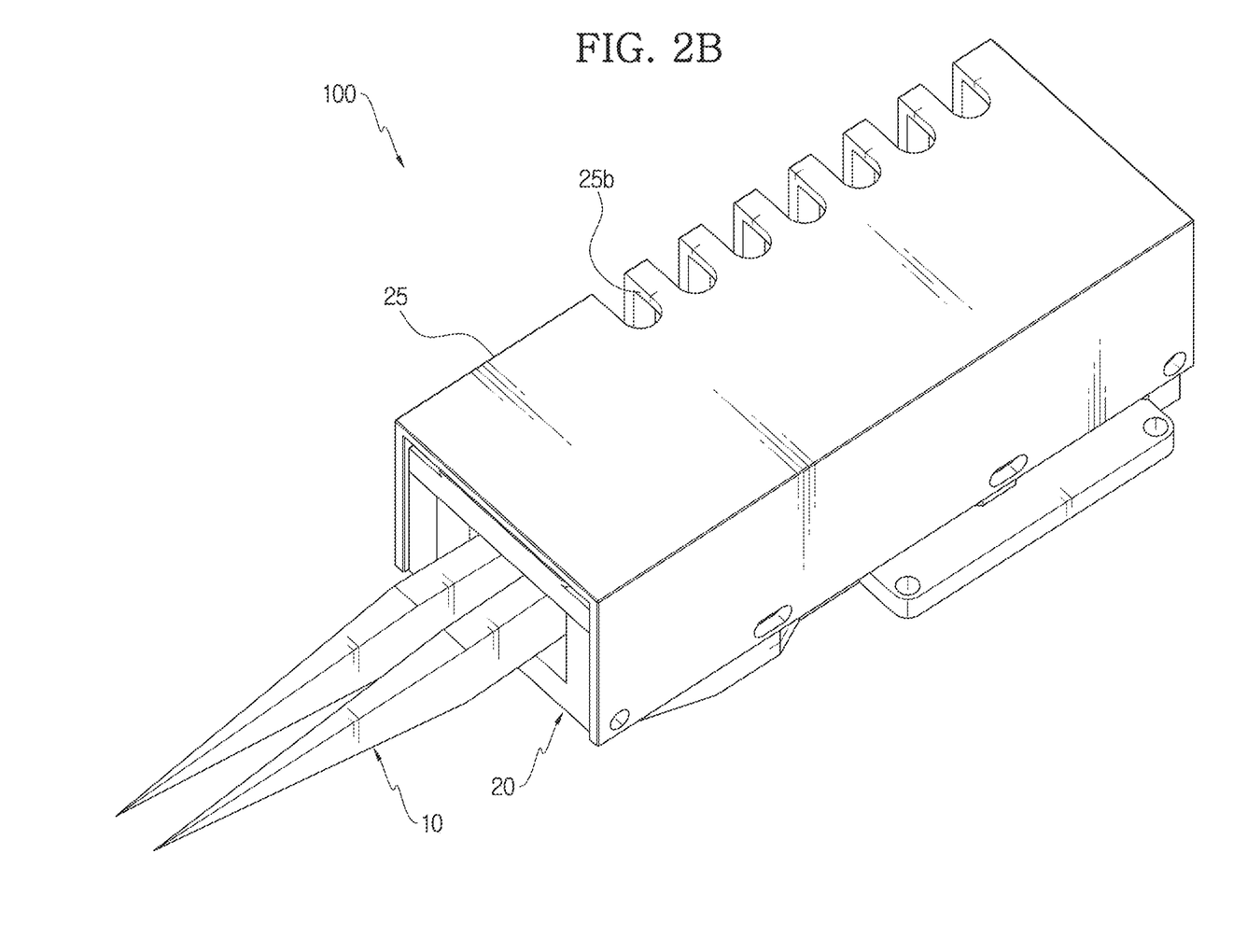
FIG. 2B is a perspective view of a forceps driving apparatus of the present disclosure including a cover.
Figure 2C:
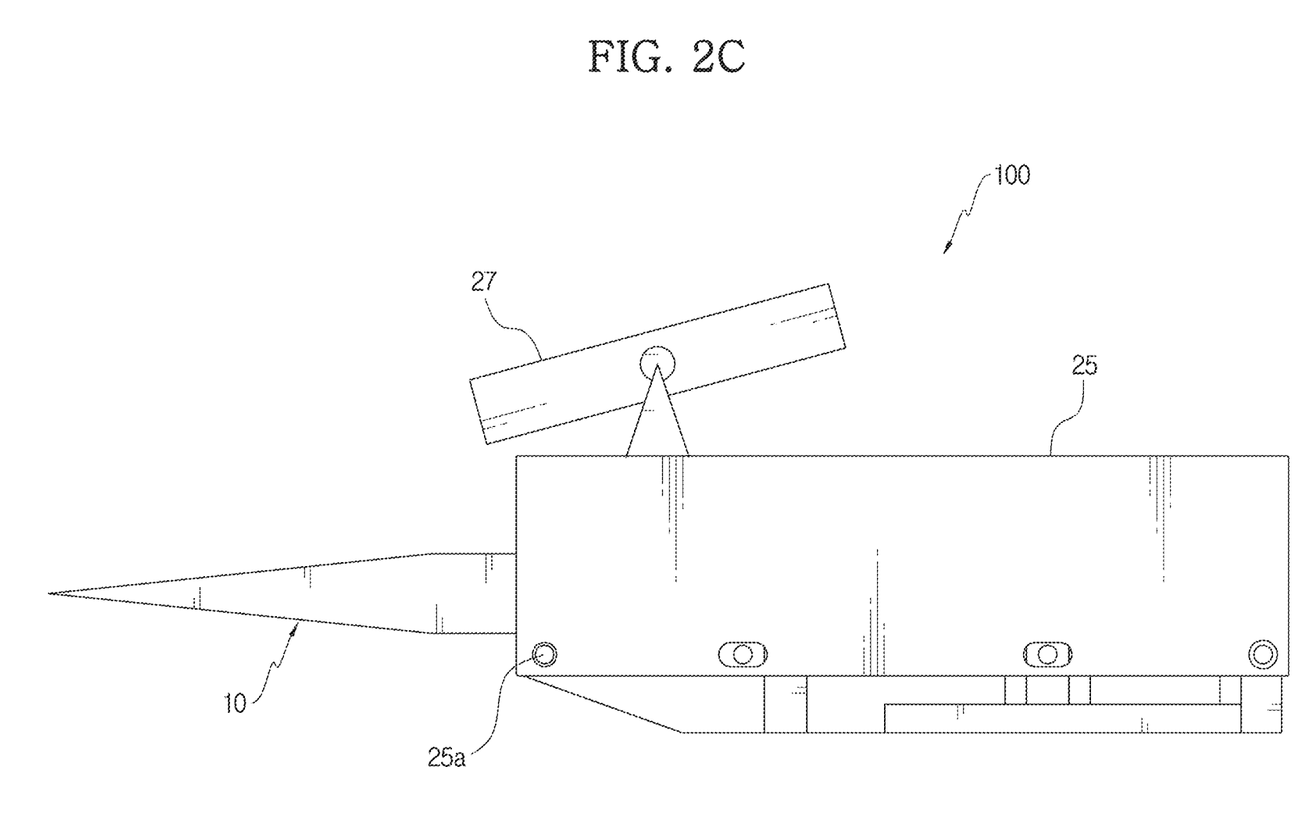
FIG. 2C is a side view of FIG. 2B further including a micro camera.

Meanwhile, FIG. 2A is a side view showing an example of operation of the forceps driving apparatus 100 of the present disclosure including a cover 25, FIG. 2B is a perspective view of the forceps driving apparatus 100 of the present disclosure including the cover 25, and FIG. 2C is a side view of FIG. 2B further including a micro camera 27.

Referring to FIG. 2A, shown is an example in which the cover 25 is installed in the body 20, and the cover 25 can rotate relative to the body 20 by a pivot 25a. The cover 25 may prevent the inner parts of the device from being contaminated during surgery. The cover 25 may be coupled to the body 20 by the magnetic force of a permanent magnet. The cover 25 is rotatable around the pivot 25a, and has one side which is detachable by the magnetic force of the permanent magnet, to easily replace or disinfect the internal components.

The cover 25 may have a heat outlet vent 25b formed by cutting as shown in FIG. 2B, and heat generated by the operation of the actuator 50 may be vented to the outdoors through the heat outlet vent 25b.

Referring to FIG. 2C, the micro camera 27 may be installed in the cover 25. The micro camera 27 may image and monitor a surgery site.

The present disclosure may use the wire type actuator as a driver, thereby achieving compact, lightweight and simple instrument designs.

The present disclosure may close the forceps by the bias spring and open the forceps by the operation of the actuator, thereby reducing power consumption.

The present disclosure may attach and detach the cover of the forceps in a simpler structure, thereby easily replacing and disinfecting the internal components.

The present disclosure may control the opening angle of the forceps through the current control.

The present disclosure may achieve fine force control, and can be used in the field of microsurgery involving gripping and manipulating the flexible microtissue.

The present disclosure may prevent the tissue from being pressed and damaged by an excessive force applied to the object.

The present disclosure may transmit a measured force to a master system capable of haptic force feedback, to allow a remote surgeon to feel the gripping of the object not only in a visual manner but also in a haptic manner.

The forceps driving apparatus 100 as described hereinabove is not limited to the configuration and method of the embodiments described above, and some or all the embodiments may be selectively combined to make various modification.

It is obvious to those skilled in the art that the present disclosure may be embodied in other particular forms without departing from the spirit and essential features of the present disclosure. Therefore, the above detailed description should not be interpreted as being limiting in all aspects and should be considered as being exemplary. The scope of the present disclosure should be determined by the reasonable interpretation of the appended claims, and the scope of the present disclosure encompasses all modifications within the equivalent scope of the present disclosure.

What is claimed is:

1. A forceps driving apparatus, comprising:
   a body;
   a gripper installed to be received in the body, and formed to be open and closed;
   an opening and closing member rotatably installed in the body to press or release two sides of the gripper by rotation;
   an elastic member connected to one side of the opening and closing member to provide an elastic force to the opening and closing member;
   an actuator connected to the another side of the opening and closing member to rotate the opening and closing member by contraction or extension; and
   a force sensing module to measure a gripping force of the gripper during the rotation of the opening and closing member;

wherein the force sensing module includes:
a sensor to measure a force transmitted when the opening and closing member presses or releases the two sides of the gripper; and
a printed circuit board (PCB) to supply the sensor with power, and receive and output information associated with the force measured by the sensor.

2. The forceps driving apparatus according to claim 1, wherein the force sensing module further includes a stress transmitter installed on one surface of the PCB and having a receiving portion in which the sensor is installed, to transmit the force when the opening and closing member presses or releases the two sides of the gripper to the sensor.

3. The forceps driving apparatus according to claim 1, wherein the gripping force of the gripper is generated when the opening and closing member presses or releases the two sides of the gripper and is calculated by calibrating the force measured by the sensor.

4. The forceps driving apparatus according to claim 1, further comprising:
a control unit to control operation of the actuator,
wherein the control unit includes:
a fuzzy controller to output proportional-integral-derivative (PID) gains; and
a PID controller to receive inputs of the PID gains from the fuzzy controller, output an amount of control, and drive the actuator based on the amount of control.

5. The forceps driving apparatus according to claim 4, wherein the control unit further includes:
a limiter to limit the output of the amount of control to prevent the amount of control from being determined in a range in which the amount of control is larger than a predetermined amount or there is no responsiveness; and
a force feedback unit to feed back a force changed by the operation of the actuator to the fuzzy controller and the PID controller.

6. A forceps driving apparatus, comprising:
a body;
a gripper installed to be received in the body, and formed to be open and closed;
an opening and closing member rotatably installed in the body to press or release two sides of the gripper by rotation;
an elastic member connected to one side of the opening and closing member to provide an elastic force to the opening and closing member;
an actuator connected to another side of the opening and closing member to rotate the opening and closing member by contraction or extension; and
a force sensing module to measure a gripping force of the gripper during the rotation of the opening and closing member;
wherein in an initial condition, the opening and closing member presses the gripper by the elastic force of the elastic member to close the gripper, and
in an operating condition, the opening and closing member releases the gripper by the contraction of the actuator to open the gripper.

7. A forceps driving apparatus, comprising:
a body;
a gripper installed to be received in the body, and formed to be open and closed;
an opening and closing member rotatably installed in the body to press or release two sides of the gripper by rotation;
an elastic member connected to one side of the opening and closing member to provide an elastic force to the opening and closing member;
an actuator connected to another side of the opening and closing member to rotate the opening and closing member by contraction or extension; and
a force sensing module to measure a gripping force of the gripper during the rotation of the opening and closing member;
wherein the gripper includes:
a first part having a first grasping end formed at one end; and
a second part having a second grasping end formed at one end, and elastically connected to another end of the first part, and
wherein the one end of the first part and the one end of the second parts are closed when pressed by the opening and closing member, and are open when released by the opening and closing member.

8. The forceps driving apparatus according to claim 7, wherein the opening and closing member includes:
a guide pin rotatably installed in the body;
a rotating plate connected to the guide pin; and
pressing members, a pressing member of the pressing members being formed at each of two sides of the rotating plate to press the first and second parts.

9. The forceps driving apparatus according to claim 8, wherein a bearing is installed between the body and the guide pin.

10. The forceps driving apparatus according to claim 8, wherein one of the pressing members has a fixing groove, and one end of the elastic member is wound on the fixing groove to provide the elastic force to the one of the pressing members, and
another of the pressing members has a fixing hole, and one end of the actuator is installed in the fixing hole to provide torque to the opening and closing member.

11. The forceps driving apparatus according to claim 8, wherein in an initial condition, the pressing members respectively press the first and second parts by the elastic force of the elastic member to close the one end of the first part and the one end of the second part, and
in an operating condition, the pressing members respectively releases the first and second parts by the contraction of the actuator to open the one end of the first part and the one end of the second part.

\* \* \* \* \*